(12) United States Patent
Schiessl et al.

(10) Patent No.: US 6,281,671 B1
(45) Date of Patent: Aug. 28, 2001

(54) ELECTRODE COMPONENT GROUP FOR A CORROSION MEASURING SYSTEM FOR DETECTING CORROSION IN A METAL EMBEDDED IN A COMPONENT MADE OF AN ION-CONDUCTING MATERIAL, IN PARTICULAR CONCRETE

(76) Inventors: Peter Schiessl, Heidweg 57, D-52076 Aachen; Michael Raupach, Parkstrasse 122, D-52027 Aachen; Klaus Kollberg, Am Berg 7, D-52146 Würselen-Euchen, all of (DE)

( * ) Notice: Subject to any disclaimer, the term of this patent is extended or adjusted under 35 U.S.C. 154(b) by 0 days.

(21) Appl. No.: 09/367,986
(22) PCT Filed: Feb. 10, 1998
(86) PCT No.: PCT/EP98/00728
§ 371 Date: Aug. 19, 1999
§ 102(e) Date: Aug. 19, 1999
(87) PCT Pub. No.: WO98/37403
PCT Pub. Date: Aug. 27, 1998

(30) Foreign Application Priority Data

Feb. 19, 1997 (DE) .............................................. 197 06 510

(51) Int. Cl.⁷ .......................... G01N 27/00; G01N 27/26; G01N 17/04; G01R 31/00; G01F 1/64
(52) U.S. Cl. .......................... 324/71.1; 324/700; 204/404; 422/53; 205/775.5; 205/777; 205/776; 205/776.5
(58) Field of Search .................................. 324/71.1, 508, 324/700; 204/404; 205/775.5, 777, 776, 776.5

(56) References Cited

U.S. PATENT DOCUMENTS

| | | | |
|---|---|---|---|
| 2,947,679 | 8/1960 | Schaschl | 204/404 |
| 3,599,090 | * 8/1971 | Fitzpatrick et al. | 324/508 |
| 3,633,099 | * 1/1972 | Richman | 324/71.7 |
| 3,772,178 | * 11/1973 | Wilson | 204/404 |
| 3,910,830 | * 10/1975 | Mayse | 204/404 |
| 3,924,175 | * 12/1975 | Wilson | 324/444 |
| 3,948,744 | * 4/1976 | Cushing | 204/404 |
| 3,980,542 | * 9/1976 | Winslow, Jr. et al. | 204/404 |

(List continued on next page.)

FOREIGN PATENT DOCUMENTS 0 364 841   4/1990   (EP) .

Primary Examiner—Glenn W. Brown
Assistant Examiner—Wasseem H. Hamdan
(74) Attorney, Agent, or Firm—Robert Becker & Assoc

(57) ABSTRACT

An electrode component group for a corrosion measuring system for detecting corrosion of a metal embedded in a construction component of ion-conducting material has a rod-shaped base body having a first flange member at a first end of base body and a second flange member at a second end of base body. The base body is insertable into the construction component with the first end leading. A plurality of spacer rings is positioned on the base body between the first and second flange members. The metal electrode rings and sealing rings are arranged alternatingly between the spacer rings. Each one of the metal electrode rings have an electrical line connected to a measuring circuit external to the construction component. The electrical lines are guided inside the metal electrode rings to the second end of the base body. A device for reducing a spacing between the first and second flange members is provided. The spacer rings, sealing rings, and metal electrode rings are designed such that, upon reduction of the spacing between the first and second flange members, sealing rings and electrode rings expand radially outwardly, so that the sealing rings and the metal electrode rings, after insertion of the electrode component group into a hole provided in the construction component, are brought into intimate contact at a wall of the hole upon reduction of the spacing between the first and second flange members.

15 Claims, 3 Drawing Sheets

U.S. PATENT DOCUMENTS

| | | | |
|---|---|---|---|
| 4,002,806 | * | 1/1977 | Gupta et al. .......................... 429/104 |
| 4,019,133 | * | 4/1977 | Manley et al. ....................... 324/700 |
| 4,109,941 | * | 8/1978 | Wood et al. .......................... 285/111 |
| 4,454,006 | * | 6/1984 | Hausler et al. ...................... 205/776 |
| 4,861,453 | | 8/1989 | Matsuoka ............................. 204/404 |
| 5,015,355 | * | 5/1991 | Schiessl .............................. 204/404 |
| 5,069,774 | * | 12/1991 | Hladky et al. ...................... 204/404 |

* cited by examiner

ELECTRODE COMPONENT GROUP FOR A CORROSION MEASURING SYSTEM FOR DETECTING CORROSION IN A METAL EMBEDDED IN A COMPONENT MADE OF AN ION-CONDUCTING MATERIAL, IN PARTICULAR CONCRETE

BACKGROUND OF THE INVENTION

The invention relates to an electrode component group for a corrosion measuring system for detecting corrosion in a metal embedded in a component made of an ion-conducting material, especially concrete.

Such ion-conducting materials, used for making components in which the electrode component group is used, are especially mineral construction components such as mortar, cement, concrete etc. Steel parts embedded in concrete, such as profiled steel supports or reinforcement inserts of construction steel, in general, are permanently protected against corrosion when the concrete construction component has been processed properly because it is protected under a sufficiently thick concrete cover. This corrosion protection is not based on the impermeability of the concrete to liquids, but resides in the alkalinity of the concrete pore water which is, in general, of a pH value of greater than 12.5. Under these conditions, on the steel surface a thin fixedly attached oxide layer will form which practically completely prevents corrosion. Accordingly, the steel reinforced concrete can be used for external construction components exposed to the elements.

Under unfavorable conditions, especially in the case of faulty construction and especially in salt-containing environmental conditions, the corrosion protection relative to the reinforcements can be lost. The reason for this may be carbonate formation of the concrete which occurs when carbon dioxide contained in the air reacts with alkaline components of the cement. As a result of this, the pH value will decrease so that no corrosion protection is present anymore. Another cause for corrosion is the penetration of chlorides into the concrete which may occur when the concrete component is used, for example, as a street surface or is in the vicinity of a street surface onto which de-icing salt has been dispensed. Such de-icing salt contains, in general, salt derived from sea water or chloride-containing salts of other origins. Both processes begin at the surface of the concrete and extend into the exterior of the concrete to the steel parts embedded therein where their oxide layer begins to dissolve. At the steel surface a critical state of increasing corrosion will result without this being noticeble at the concrete surface. The corrosion damage is, in general, only then recognized when the corrosion of the steel has progressed and the pressure of the rust products causes the concrete layer to chip off.

From EP 0 364 841 B1 a corrosion measuring system for determining corrosion of steel embedded in concrete construction components is known which comprises a multiple anode electrodes arranged spaced apart from one another within the concrete construction component and comprised of regular construction steel. They are arranged at different depths in the concrete construction component and are electrically connected to at least one cathode electrode by a measuring circuit accessible from the exterior, whereby the cathode electrode is comprised of a more noble material. By electrically connecting one of the anode electrodes with the cathode electrode, the corrosion state of the respective anode electrode and thus the progress of corrosion in the concrete construction component can be determined. In the known corrosion measuring system, it is necessary to integrate the individual anode electrode and cathode electrodes during manufacture of the concrete construction component which does not allow for subsequent corrosion testing of concrete construction components which have not been provided initially with such a corrosion measuring system.

From U.S. Pat. No. 2,947,679 an arrangement for determining the corrosion rate of different materials is known. At the outer surface of a tubular support member electrode rings of the materials to be tested are arranged spaced to one another. At one end of the tubular support member, comprised of insulating material, a reference electrode is arranged. All electrodes are provided with lines which are guided through the interior of the tubular support member and are connectable to a measuring circuit. The entire arrangement can be inserted into a bath containing a corroding liquid, for example, an acidic aqueous solution. By electrically connecting the different measuring electrodes to the reference electrode, the different corrosion of the measuring electrodes can be determined. An introduction of this system directly into a concrete construction component is not envisioned.

It is an object of the invention to provide an electrode component group for a corrosion measuring system for determining corrosion of a metal embedded in a concrete construction component which electrode component group can be retrofitted in a simple manner into a concrete construction component whose corrosion is to be measured.

SUMMARY OF THE INVENTION

With the inventive electrode component group that can be retrofitted into a hole or a bore of the component a safe, large surface area, and permanent contact between the electrode rings and the concrete is achieved. By means of the sealing rings positioned between the electrode rings and resting sealingly at the construction component, geometric measuring areas are provided which are separated from one another and are correlated with a respective electrode ring so that a precise corrosion analysis is possible.

Advantageous further embodiments of the inventive electrode component group are provided in the dependent claims.

BRIEF DESCRIPTION OF THE DRAWINGS

The invention will be explained in the following with the aid of schematic drawings in an exemplary manner and with further details.

It is shown in.

DESCRIPTION OF PREFERRED EMBODIMENTS

Figure 1:
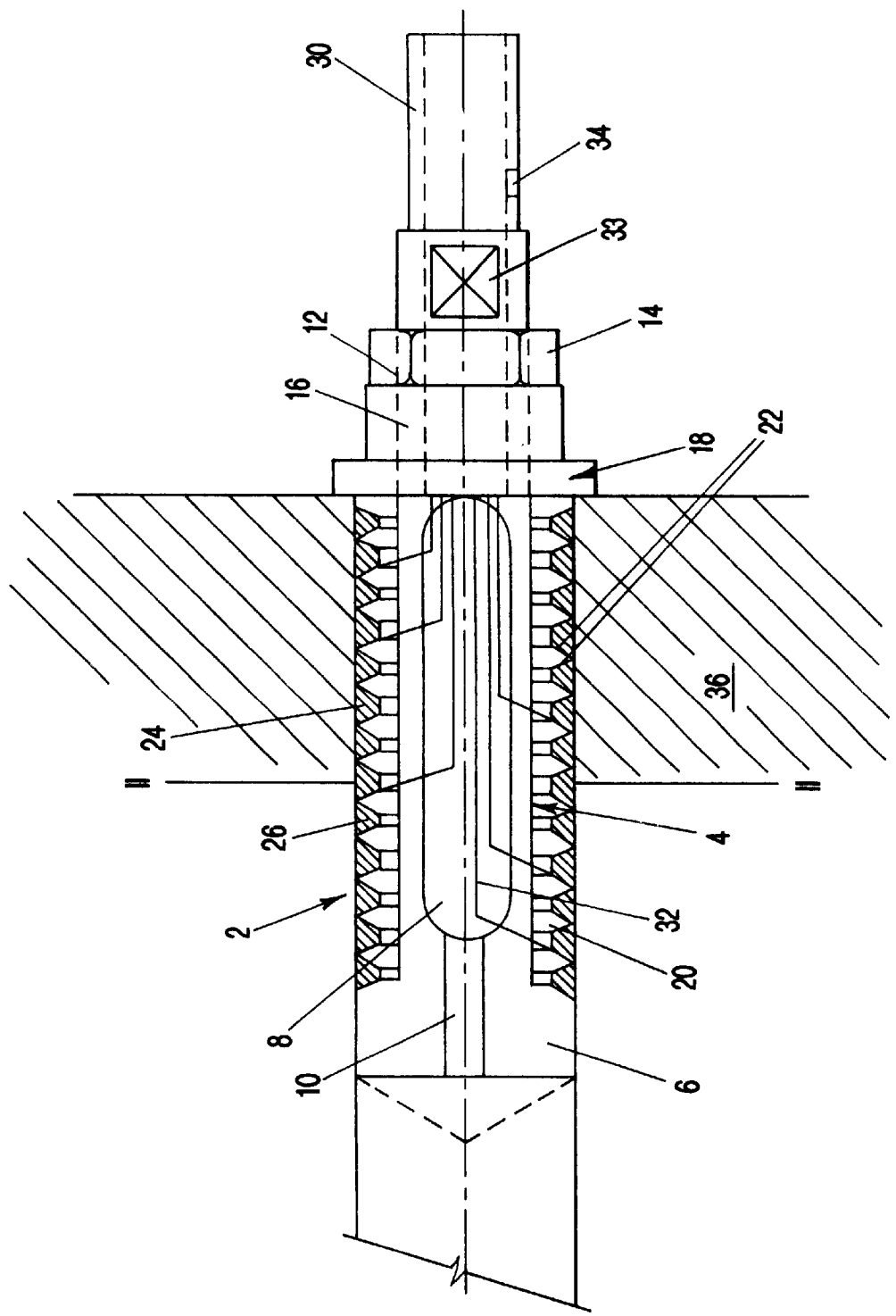
FIG. 1 a longitudinal section of a first embodiment of an electrode component group.

According to FIG. 1, the electrode component group identified by 2 comprises a rod-shaped base body 4 which is a support member for the entire arrangement and ends to the left of the figure in a flange member 6 with widened diameter. The base body 4 has a recessed, respectively, a longitudinal slot 8 from where a through channel 10 extends to the flange member 6.

At a spacing from the flange member 6 the base body 4 has a threaded area 12 onto which a nut 14 is threaded. From the interior of the base body a channel 16 extends through the base body to the right end shown in FIG. 1. The nut 14 rests, optionally with intermediate arrangement of a washer, at a clamping flange 18 which is longitudinally slidably arranged on the support member 4 and has an outer diameter that is greater than that of the flange member 6.

The base body 4 supports between the flange members 6 and 18 a plurality of spacer rings 20 having lateral surfaces ending, in a direction toward an outer circumference, in slanted surfaces 22. Between two spacer rings 20 electrode rings 24 and sealing rings 26 are arranged alternatingly whereby preferably between the respective outermost spacer rings 20 and the flange member 6 or 18 a sealing ring is arranged.

The sealing rings, comprised of elastic and electrically insulated material, have preferably a round cross-section. The electrode rings 24, comprised preferably of construction steel, have a trapezoid cross-section whereby the slant of its lateral surfaces matches the slant of the slanted surfaces 22.

The size of the spacer rings 20, electrode rings 24, and sealing rings 26 is such that the outer circumference in the loose state of the arrangement does not project past the outer circumference of the flange member 6.

Opposite the nut 14, the base body 4 ends in a bushing 30 in which one electrical line 32 for each one of the electrode rings 24 is connected to a contact (not shown). The lines 32 are guided through the longitudinal slot 8 into the interior of the support member 4.

External to the nut 14 the base body has flattened portions 33 for attachment of a tool, for example, a wrench. Furthermore, a radial opening 34 is provided through which the channel 16 is accessible. The entire arrangement is inserted into a bore 35 which is provided in a concrete construction component 36 and has an inner diameter which corresponds substantially to the outer diameter of the flange member 6.

The assembly of the afore disclosed arrangement is as follows.

Figure 2:
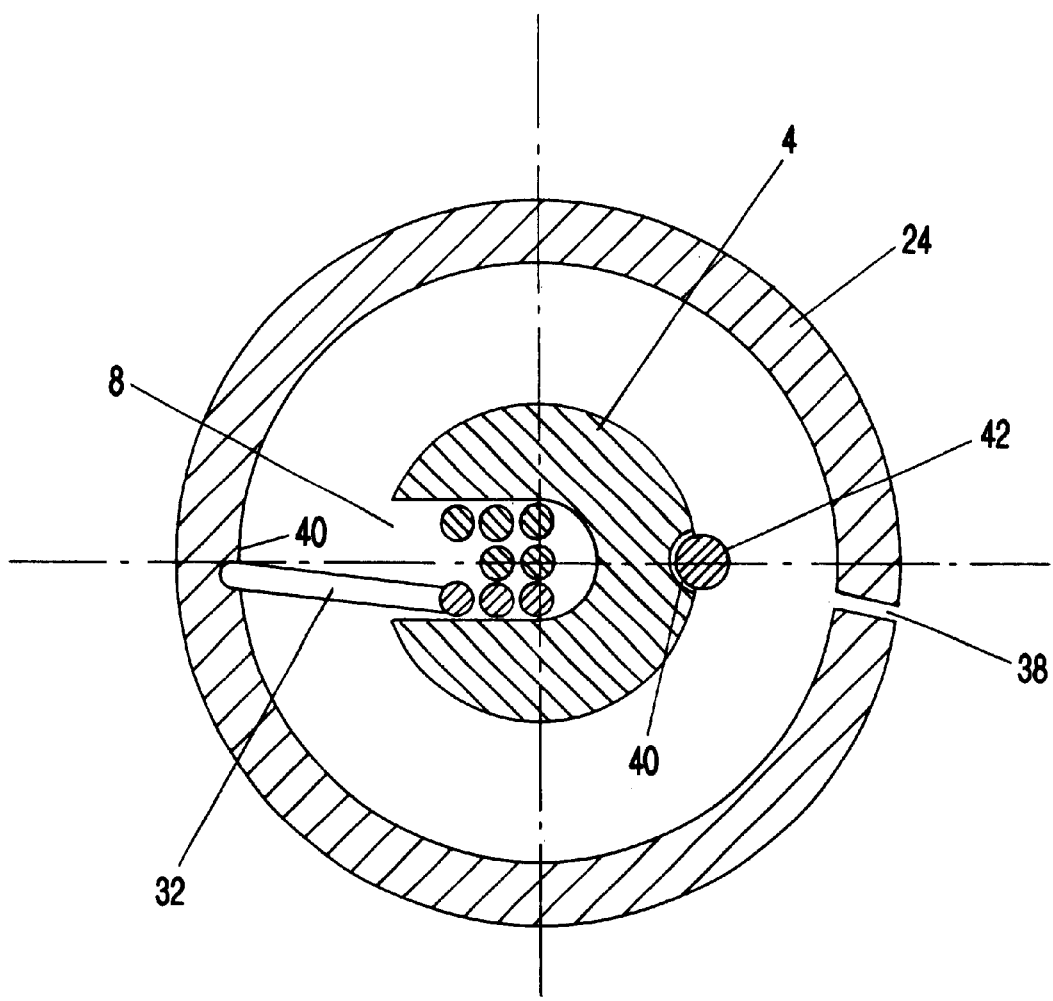
FIG. 2 a cross-section of the electrode component group according to FIG. 1, according to section plane II—II.

The sealing rings 26, spacer rings 20, and electrode rings 24 are first slipped onto the base body 4 in the aforementioned sequence. The lines 32 connected to the electrode rings 24, for example, by soldering, are introduced into the longitudinal slot 8 and pushed through the channel 16 so that they project from the right side. The clamping flange 18 is pushed onto the base body 4, and the nut 14 is then screwed on so that the rings are secured between the flange members 6 and 18 on the base body 4. The lines 32 are connected to the connector bushing 30 which is fastened to the base body 4. The arrangement is now complete for mounting in a bore 35 of the concrete construction component 36. For this purpose, the arrangement, with the flange member 6 leading, is inserted into the bore 35 until the clamping flange 18 abuts the external side of the concrete construction component 36. Advantageously, between the clamping flange 18 and the concrete construction component 36 a seal (not represented in FIG. 1) is positioned. The nut 14 is now rotated whereby the base body 4 is secured at the flattened portion 33 by a wrench. The flange member 6 is moved to the right of FIG. 1 together with the base body 4 so that the spacing between the flange member 6 and the clamping flange 18 is reduced. The spacing between the spacer rings 20 is also reduced so that the sealing rings 26 and the electrode rings 24 are moved outwardly, respectively, are spreaded. The size of the slanted surfaces 22 of the spacer rings 20 relative to the sealing rings 26 is such that the spacer rings 20 will come into direct contact with one another before the sealing rings 26 are outwardly spread to unacceptable limits that could cause damage. The sealing rings 26 are thus brought into perfect abutment at the inner wall of the bore 35 and seal individual bore segments relative to one another. Upon further tightening of the nut 14, the electrode rings 24 which will spread only with application of greater forces in comparison to the sealing rings 26, are spread, respectively, enlarged with regard to the outer diameter so that they are also in a fixed contact at the inner wall of the bore 35. The electrode rings 24 can be slotted for facilitating the spreading action (FIG. 2). For intensifying the contact between the outer circumference of the electrode rings 24 and the inner wall of the bore 35, the outer circumference of the electrode rings 24 are provided with fluting or knurling. The entire arrangement, for sufficient tightening of the nut 14, is secure and safely held with inner contact in the bore 35. Subsequently, a specialty grease is pressed through the opening 34 into the interior of the base body 4 which fills the space between the rings and can enter the bore 35 through the channel 10. The transition area from the connecting bushing 30 to the support member 4 and the opening 34 is then closed by cast resin so that the entire arrangement is hermetically sealed to the exterior.

The electrode component group 2 inserted into the bore 35 and fastened therein thus provides a sensor divided into separate measuring chambers whereby each measuring chamber contains an electrode ring 24 by which the introduction of pollutants into the concrete can be followed in a stepwise manner since the individual electrode rings are connected in a manner known to a person skilled in the art to a measuring circuit. A cathode of stainless steel or titanium coated with platinum oxide can be used as a counter electrode inserted into the concrete construction part 36. The individual electrode rings 24 can also electrically connected to one another so that for different corrosion states measurable currents will flow. Alternatively, one of the electrode rings 24 can be comprised of noble metal and can serve as a cathode. It is understood that the electrode rings 24 are preferably comprised of the same material as the reinforcement of the concrete construction component 36 whose corrosion state is to be detected. The coupling of electrode rings 24 to the concrete can be realized by direct AC current resistance measurement between the electrode rings 24. As mentioned above, with the disclosed spreading of the rings closed measuring zones are provided in predetermined positions so that, for example, chloride can reach the electrode rings only laterally from the exterior and no chloride transport along the walls of the bore 35 is possible.

The inner sealing action of the entire arrangement ensures a corrosion protection its metal parts. In the area of the connecting bushing 30 a resin fill is provided which is electrically insulated and rigid. In the area of the rings pressure application with grease is provided so that the grease extends into the bore hole.

It is understood that the electrode rings 24 must not be in electrical contact with one another via the spacer rings 20 and the base body 4. This can be realized by an expedient selection of materials, for example, by embodying the base body 4 or the spacer rings 20 of plastic or by providing a respective coating thereon. It is understood that for avoiding overload of the sealing rings 26 the spacer rings 20 must be provided with respective lateral projections which ensure the required spacing.

FIG. 2 shows a cross-sectional view of the arrangement of FIG. 1. A slot 38 of the electrode ring 24 is shown which facilitates spreading but must not be present for an electrode ring which is sufficiently yielding. Also shown is a soldering connection 40 of the line 32 to the electrode ring 24. The base body 4 is provided with a longitudinal groove 40 which receives a rod 42 comprised, for example, of PVC which engages corresponding recesses of the spacer rings to secure them against rotation (not shown in FIG. 1). The rotational securing action can also be realized by a projection extending along the base body 4 which engages a corresponding recesses of the spacer rings 20 and also optionally of the clamping flange 18.

Figure 3:
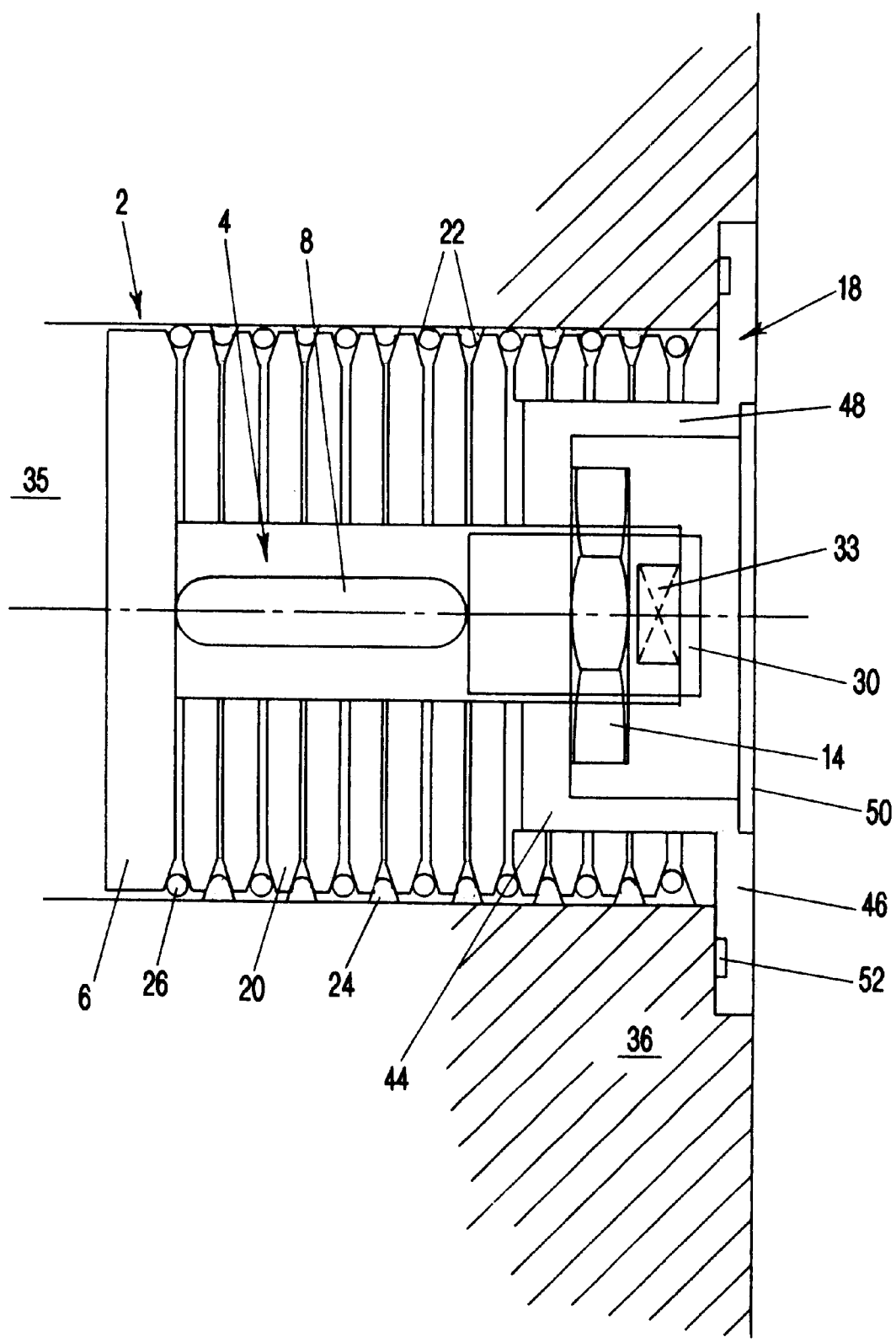
FIG. 3 a longitudinal section of a second embodiment of the electrode component group.

FIG. 3 shows a different embodiment of the electrode component group of FIG. 1.

The clamping flange 18 is hat-shaped and comprises an inner bottom 44 and an outer edge flange 46 having a transition into one another by a cylindrical area 48. The rings 20, 24, and 26 are embodied such that they are supported partially by the base body 4 and partially by the cylindrical area 48. The connecting bushing 30 provided at one end of the base body 4 is received in the interior of the hat-shaped clamping flange 48 so that this interior can be covered by a cap 50. The edge flange 46 is inserted into the recess of the concrete construction component 36 provided at the edge of the bore 35 with interposition of sealing ring 52 so that the entire arrangement is flush to the exterior. Upon use, the cap 50 is removed and a known measuring circuit is connected to the connecting bushing 30 which optionally comprises a cathode electrode separate from the electrode component group 2 and inserted into the concrete construction component 36.

The present invention is, of course, in no way restricted to the specific disclosure of the specification and drawings, but also encompasses any modifications within the scope of the appended claims.

What is claimed is:

1. An electrode component group for a corrosion measuring system for detecting corrosion of a metal embedded in a construction component of ion-conducting material, said electrode component group comprising:

a rod-shaped base body (4) having a first flange member (6) at a first end of said base body (4) and a second flange member (18) at a second end of said base body (4), wherein said base body (4) is insertable into the construction component with. said first end leading;

a plurality of spacer rings (20) positioned on said base body (4) between said first and second flange members (6, 18);

metal electrode rings (24) and sealing rings (26) arranged alternatingly between said spacer rings (20);

each one of said metal electrode rings (24) having an electrical line (32) connectable to a measuring circuit external to the construction component;

said electrical lines (32) guided inside said metal electrode rings (24) through an interior of said base body to said second end of said base body (4);

a device (12, 14) for reducing a spacing between said first and second flange members (6, 18);

said spacer rings (22), said sealing rings (26), and said metal electrode rings (24) designed such that, upon reduction of said spacing between said first and second flange members (6, 18), said sealing rings (26) and said electrode rings (24) expand radially outwardly, so that said sealing rings (26) and said metal electrode rings (24), after insertion of said electrode component group into a hole (34) provided in the construction component, are brought into intimate contact at a wall of the hole upon reduction of said spacing between said first and second flange members (6, 18).

2. An electrode component group according to claim 1, wherein said metal electrode rings (24) and the metal embedded in the construction component are comprised of identical metal material.

3. An electrode component group according to claim 1, wherein said sealing rings (26) and said spacer rings (20) are matched to one another such that a radial expansion of said sealing rings (26) is limited by said spacer rings (20) abutting one another upon reduction of said spacing between said flange members (6, 18).

4. An electrode component group according to claim 1, wherein said sealing rings (26) have a circular cross-section.

5. An electrode component group according to claim 1, wherein said electrode rings (24) have a trapezoidal cross-section having lateral surfaces, wherein said lateral surfaces of said electrode rings (24) have a slant matching a slant of radially outer lateral surfaces (22) of said spacer rings (20).

6. An electrode component group according to claim 1, wherein said electrode rings (24) have a knurled outer circumference.

7. An electrode component group according to claim 1, wherein said device for reducing said spacing between said first and second flange members (6, 18) comprises a nut (14) and wherein said base body (4) has a threaded area (12) projecting from said second flange member (18), wherein said nut (14) is threaded onto said threaded area (12) and wherein said second flange member (18) is movable along said base body (4) by said nut (14).

8. An electrode component group according to claim 7, wherein said second flange member (18) is hat-shaped.

9. An electrode component group according to claim 7, wherein said second flange member (18) has an end face facing away from said nut (14) and wherein said end face has a seal (48).

10. An electrode component group according to claim 9, wherein one of said first and second flange members (18) is hat-shaped and has an interior covered by a cap (50), wherein said connecting bushing (30) is arranged in said interior of said flange member (18) and is covered by said cap (50).

11. An electrode component group according to claim 1, further comprising a connecting bushing (30) connected to said second end of said base body (4) that is positioned external to the construction component.

12. An electrode component group according to claim 1, wherein said base body (4) has a hollow interior and has a longitudinal slot (8), wherein said electrical lines (32) are guided through said longitudinal slot (8) into said hollow interior.

13. An electrode component group according to claim 12, wherein said base body (4) has a through channel (10) at said first end and wherein said hollow interior of said base body (4) is filled with grease introduced via said through channel (10).

14. An electrode component group according to claim 13, further comprising a means (40, 42) for securing said base body (4) and said spacer rings (20) against rotation.

15. An electrode component group according to claim 1, wherein said means (40, 42) secures said second flange member (18) relative to said base body (4) so that no relative rotation between said second flange member (18) and said base body (4) is possible.

* * * * *